United States Patent
Patil et al.

(10) Patent No.: US 11,823,354 B2
(45) Date of Patent: Nov. 21, 2023

(54) SYSTEM AND METHOD FOR UTILIZING A DEEP LEARNING NETWORK TO CORRECT FOR A BAD PIXEL IN A COMPUTED TOMOGRAPHY DETECTOR

(71) Applicant: GE PRECISION HEALTHCARE LLC, Wauwatosa, WI (US)

(72) Inventors: Bhushan Dayaram Patil, Pune (IN);
Rajesh Langoju, Bangalore (IN);
Utkarsh Agrawal, Bangalore (IN);
Bipul Das, Chennai (IN); Jiang Hsieh, Brookfield, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 292 days.

(21) Appl. No.: 17/225,395

(22) Filed: Apr. 8, 2021

(65) Prior Publication Data
US 2022/0327664 A1    Oct. 13, 2022

(51) Int. Cl.
*G06T 5/00*    (2006.01)
*G16H 30/20*    (2018.01)
(Continued)

(52) U.S. Cl.
CPC .............. *G06T 5/002* (2013.01); *G06N 3/08* (2013.01); *G06T 11/008* (2013.01); *G16H 30/20* (2018.01);
(Continued)

(58) Field of Classification Search
CPC ................... G06T 5/002; G06T 11/008; G06T 2207/10081; G06T 2207/20081;
(Continued)

(56) References Cited

U.S. PATENT DOCUMENTS 7,602,951 B2    10/2009 Hsieh et al.
7,920,751 B2    4/2011 Li et al.
(Continued)

FOREIGN PATENT DOCUMENTS

| CN | 110555834 A | 12/2019 |
| JP | 2021013726 A | 2/2021 |
| JP | 2021034752 A | 3/2021 |

OTHER PUBLICATIONS

Lee Eunae et al: "Using deep learning for pixel-defect corrections in flat-panel radiography imaging", Journal of Medical Imaging, Society of Photo-Optical Instrumentationengineers, 1000 20th St. Wellingham WA 98225-6705 USA, vol. 8, No. 2, Mar. 4, 2021 (Mar. 4, 2021), p. 23501. (Year: 2021).*

(Continued)

*Primary Examiner* — Van D Huynh
(74) *Attorney, Agent, or Firm* — Fletcher Yoder P.C.

(57) ABSTRACT

A computer-implemented method for correcting artifacts in computed tomography data is provided. The method includes inputting a sinogram into a trained sinogram correction network, wherein the sinogram is missing a pixel value for at least one pixel. The method also includes processing the sinogram via one or more layers of the trained sinogram correction network, wherein processing the sinogram includes deriving complementary information from the sinogram and estimating the pixel value for the at least one pixel based on the complementary information. The method further includes outputting from the trained sinogram correction network a corrected sinogram having the estimated pixel value.

18 Claims, 7 Drawing Sheets

(51) Int. Cl.
  *G06N 3/08* (2023.01)
  *G06T 11/00* (2006.01)
(52) U.S. Cl.
  CPC .............. *G06T 2207/10081* (2013.01); *G06T 2207/20081* (2013.01); *G06T 2207/20084* (2013.01); *G06T 2211/408* (2013.01)
(58) Field of Classification Search
  CPC ..... G06T 2207/20084; G06T 2211/408; G06T 5/005; G06T 11/005; G06N 3/08; G06N 3/084; G16H 30/20
  USPC ........................................................ 382/131
  See application file for complete search history.

(56) References Cited

U.S. PATENT DOCUMENTS

| | | | |
|---|---|---|---|
| 8,699,811 B2 | 4/2014 | Li et al. | |
| 10,825,149 B2 | 11/2020 | Schafer et al. | |
| 11,100,684 B2 | 8/2021 | Hein | |
| 11,367,000 B2 | 6/2022 | Takeshima | |
| 2019/0328348 A1* | 10/2019 | De Man | G06T 5/20 |
| 2020/0065945 A1* | 2/2020 | Schafer | G06T 5/005 |
| 2020/0196972 A1* | 6/2020 | Zhou | G06T 11/006 |
| 2020/0311490 A1* | 10/2020 | Lee | G01T 1/17 |
| 2020/0390414 A1 | 12/2020 | Ikhlef et al. | |
| 2021/0012543 A1* | 1/2021 | Hein | G06T 11/008 |
| 2022/0207680 A1* | 6/2022 | Wang | G06N 3/045 |

OTHER PUBLICATIONS

EP patent application 22165792.7 filed Mar. 31, 2022—extended Search Report dated Sep. 2, 2022; 8 pages.

Lee Eunae et al: "Using deep learning for pixel defect corrections in flat-panel radiography imaging", Journal of Medical Imaging, Society of Photo-Optical Instrumentation Engineers, 1000 20th St. Bellingham WA 98225-6705 USA, vol. 8, No. 2, Mar. 4, 2021 (Mar. 4, 2021), p. 23501, XP060139919, ISSN: 2329-4302, DOI: 10.1117/1.JMI.8.2.023501; [retrieved on Mar. 4, 2021].

JP application 2022-061508 filed Apr. 1, 2022—Office Action dated Mar. 8, 2023; Machine Translation; 8 pages.

* cited by examiner

SYSTEM AND METHOD FOR UTILIZING A DEEP LEARNING NETWORK TO CORRECT FOR A BAD PIXEL IN A COMPUTED TOMOGRAPHY DETECTOR

BACKGROUND

The subject matter disclosed herein relates to medical imaging and, more particularly, to systems and methods for utilizing a deep learning network for correcting for a bad pixel in a computed tomography detector.

Non-invasive imaging technologies allow images of the internal structures or features of a subject (patient, manufactured good, baggage, package, or passenger) to be obtained non-invasively. In particular, such non-invasive imaging technologies rely on various physical principles, such as the differential transmission of X-rays through the target volume or the reflection of acoustic waves, to acquire data and to construct images or otherwise represent the internal features of the subject.

For example, in X-ray-based imaging technologies, a subject of interest, such as a human patient, is irradiated with X-ray radiation and the attenuated radiation impacts a detector where the attenuated intensity data is collected. In digital X-ray systems, a detector produces signals representative of the amount or intensity of radiation impacting discrete pixel regions of a detector surface. The signals may then be processed to generate an image that may be displayed for review.

In one such X-ray based technique, known as computed tomography (CT), a scanner may project fan-shaped or cone-shaped X-ray beams from an X-ray source from numerous view-angle positions on an object being imaged, such as a patient. The X-ray beams are attenuated as they traverse the object and are detected by a set of detector elements which produce signals representing the intensity of the attenuated X-ray radiation on the detector. The signals are processed to produce data representing the line integrals of the linear attenuation coefficients of the object along the X-ray paths. These signals are typically called "projection data" or just "projections". By using reconstruction techniques, such as filtered backprojection, images may be generated that represent a volume or a volumetric rendering of a region of interest of the patient or imaged object. In a medical context, pathologies or other structures of interest may then be located or identified from the reconstructed images or rendered volume.

A bad pixel in the detector may result in missing data in the sinogram domain of the acquired CT data and undesirable artifacts (ring and streak) in the reconstructed image or volume. In addition, having a bad pixel in the CT detector impacts the ability to utilize a CT system. For example, a single bad pixel in isocenter of the CT detector keeps the CT system from being utilized. A certain number of bad pixels in the CT detector also keeps the CT system from being utilized.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a computer-implemented method for correcting artifacts in computed tomography data is provided. The method includes inputting a sinogram into a trained sinogram correction network, wherein the sinogram is missing a pixel value for at least one pixel. The method also includes processing the sinogram via one or more layers of the trained sinogram correction network, wherein processing the sinogram includes deriving complementary information from the sinogram and estimating the pixel value for the at least one pixel based on the complementary information. The method further includes outputting from the trained sinogram correction network a corrected sinogram having the estimated pixel value.

In another embodiment, a computer-implemented method for generating a trained neural network to estimate missing values in computed tomography data is provided. The method includes providing training data including sinograms and complementary information derived from the sinograms, wherein the sinograms include sinograms without any missing pixel values and corresponding sinograms with missing pixel values simulated from the sinograms without any missing pixel values. The method also includes training, using the training data, a neural network to correct a sinogram having a pixel value missing for at least one pixel based on utilizing a combined training loss derived from both the sinogram domain of the training data and an image reconstruction domain of images reconstructed from the training data.

In a further embodiment, a deep learning-based sinogram correction system is provided. The system includes a memory encoding processor-executable routines. The system also includes a processing component configured to access the memory and to execute the processor-executable routines, wherein the routines, when executed by the processing component, cause the processing component to perform acts. The acts include inputting a sinogram into a trained sinogram correction network, wherein the sinogram is missing a pixel value for at least one pixel. The acts also include processing the sinogram via one or more layers of the trained sinogram correction network, wherein processing the sinogram includes deriving complementary information from the sinogram and estimating the pixel value for the at least one pixel based on the complementary information, wherein the complementary information includes multi-channel patches, and the multi-channel patches include a local neighborhood patch from the sinogram corresponding to a portion along a channel-view direction of a row having the at least one pixel a neighboring row patch from the sinogram corresponding to an adjacent row to the row having the at least one pixel, and a conjugate patch from the sinogram corresponding to a conjugate region relative to the at least one pixel. The acts further include outputting from the trained sinogram correction network a corrected sinogram having the estimated pixel value.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
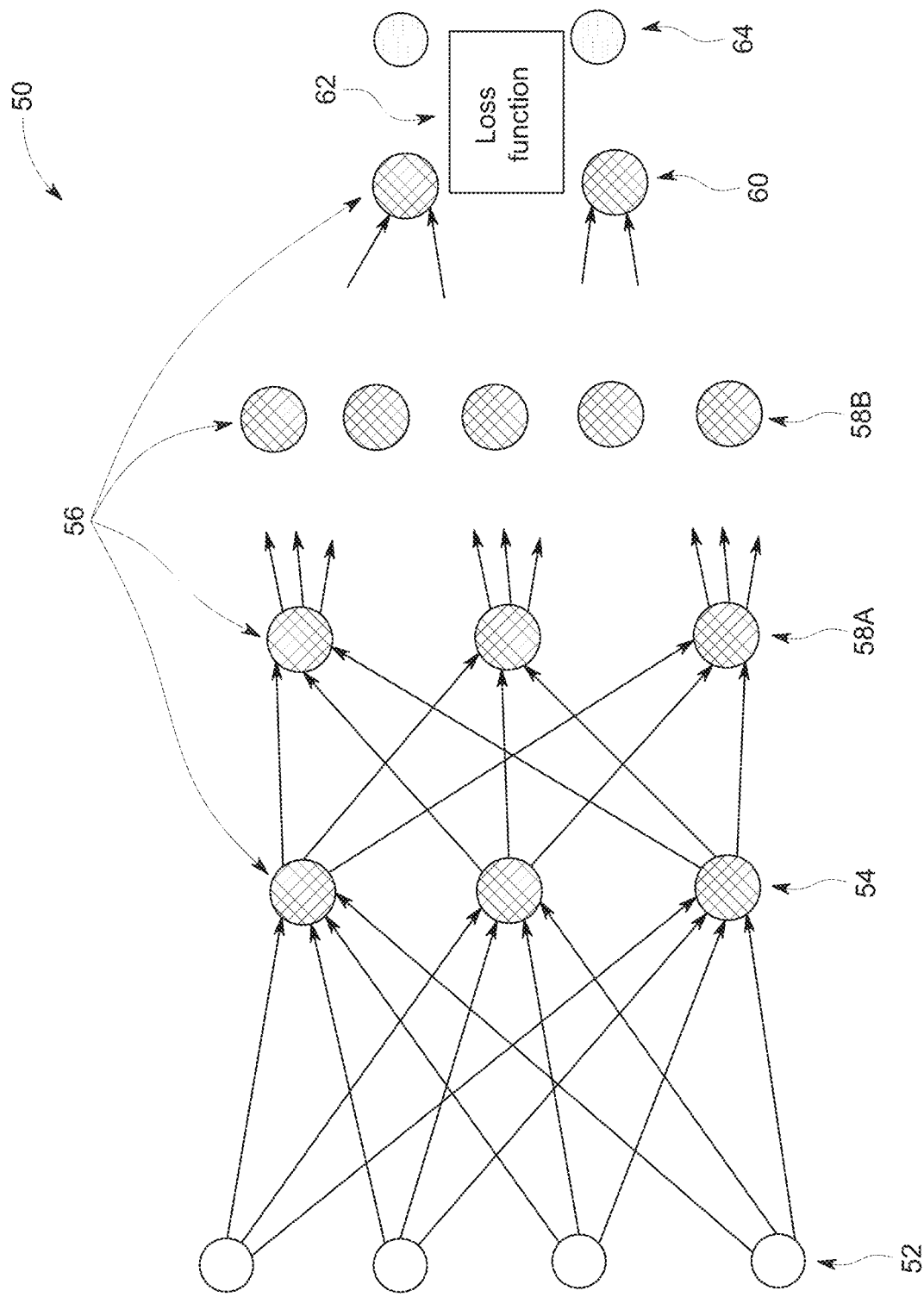
FIG. 1 depicts an example of an artificial neural network for training a deep learning model, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion are provided in the context of medical imaging, it should be appreciated that the present techniques are not limited to such medical contexts. Indeed, the provision of examples and explanations in such a medical context is only to facilitate discussion by providing instances of real-world implementations and applications. However, the present approaches may also be utilized in other contexts, such as industrial computed tomography (CT) used in non-destructive inspection of manufactured parts or goods (i.e., quality control or quality review applications), and/or the non-invasive inspection of packages, boxes, luggage, and so forth (i.e., security or screening applications).

As discussed herein, artifacts (ring, streak, etc.) found in CT images can be symptomatic of CT component issues. For example, a bad pixel in the CT detector may cause a ring artifact (rings centered within the center of rotation) leading to structured non-uniformities and deterioration of image quality. The rings make the CT images unusable for diagnostic purposes. In addition, if the number of bad pixels is above a certain threshold or if a bad pixel is located within a central region (system isocenter) of the CT detector, it may result in large service costs and, possibly, replacement of the CT detector.

The approach discussed herein addresses these issues by applying deep learning methods (e.g., convolutional neural networks or multilayer perceptrons) utilizing supervised learning to remove these artifacts due to the one or more bad pixels. The deep learning algorithm works in both the raw sinogram domain and the reconstruction domain to learn to remove the distortions caused by the bad pixels. In particular, the deep learning algorithm learns to remove the artifacts created by the bad pixels by learning a correlation between complementary information within the sinogram domain data. For example, in one implementation a deep neural network (or other suitable machine learning architecture) may be employed in this process. As may be appreciated, a neural network as discussed herein can be trained for use across multiple types of configurations (e.g., axial or helical scan (different pitch), varying kV/mA ratings, detector size, or bad pixel configuration (single or multiple pixels within separate or group locations)). Further, in some embodiments, more than one neural network may be utilized.

With the preceding in mind, neural networks as discussed herein may encompass deep neural networks, fully connected networks, convolutional neural networks (CNNs), perceptrons (e.g., multilayer perceptrons (MLPs)), auto encoders, recurrent networks, wavelet filter banks, or other neural network architectures. These techniques are generally referred to herein as machine learning. As discussed herein, one implementation of machine learning may be deep learning techniques, and such deep learning terminology may also be used specifically in reference to the use of deep neural networks, which is a neural network having a plurality of layers.

As discussed herein, deep learning techniques (which may also be known as deep machine learning, hierarchical learning, or deep structured learning) are a branch of machine learning techniques that employ mathematical representations of data and artificial neural network for learning. By way of example, deep learning approaches may be characterized by their use of one or more algorithms to extract or model high level abstractions of a type of data of interest. This may be accomplished using one or more processing layers, with each layer typically corresponding to a different level of abstraction or a different stage or phase of a process or event and, therefore potentially employing or utilizing different aspects of the initial data or outputs of a preceding layer (i.e., a hierarchy or cascade of layers) as the target of the processes or algorithms of a given layer. In an image processing or reconstruction context, this may be characterized as different layers corresponding to the different feature levels or resolution in the data. In general, the processing from one representation space to the next-level representation space can be considered as one 'stage' of the process. Each stage of the reconstruction can be performed by separate neural networks or by different parts of one larger neural network.

As discussed herein, as part of the initial training of deep learning processes to solve a particular problem, such as identification of service issues based on identified artifacts in image data, training data sets may be employed that have known initial values (e.g., input images, projection data (e.g., sinograms with or without missing values for bad pixels in the detector), and so forth) and known or desired values for a final output (e.g., corrected sinograms, reconstructed tomographic reconstructions, such as cross-sectional images or volumetric representations). The training of a single stage may have known input values corresponding to one representation space and known output values corresponding to a next-level representation space. In this manner, the deep learning algorithms may process (in a supervised manner, i.e., all of the training data is completely labeled) the known or training data sets until the mathematical relationships between the initial data and desired output(s) are discerned and/or the mathematical relationships between the inputs and outputs of each layer are discerned and characterized. Similarly, separate validation data sets may be employed in which both the initial and desired target values are known, but only the initial values are supplied to the trained deep learning algorithms, with the outputs then being compared to the outputs of the deep learning algorithm to validate the prior training and/or to prevent overtraining.

With the preceding in mind, FIG. 1 schematically depicts an example of an artificial neural network 50 that may be trained as a deep learning model as discussed herein. In this example, the network 50 is multi-layered, with a training input 52 and multiple layers including an input layer 54, hidden layers 58A, 58B, and so forth, and an output layer 60 and the training target 64 present in the network 50. Each layer, in this example, is composed of a plurality of "neurons" or nodes 56. The number of neurons 56 may be constant between layers or, as depicted, may vary from layer to layer. Neurons 56 at each layer generate respective outputs that serve as inputs to the neurons 56 of the next hierarchical layer. In practice, a weighted sum of the inputs with an added bias is computed to "excite" or "activate" each respective neuron of the layers according to an activation function, such as rectified linear unit (ReLU), sigmoid function, hyperbolic tangent function, or otherwise specified or programmed. The outputs of the final layer constitute the network output 60 (e.g., one or more convolution kernel parameters, a convolution kernel, and so forth) which, in conjunction with the training target 64, are used to compute some loss or error function 62, which will be backpropagated to guide the network training.

The loss or error function 62 measures the difference between the network output (e.g., a convolution kernel or kernel parameter) and the training target. In certain implementations, the loss function may be a mean absolute error (MAE) (e.g., between a measured sinogram and a corrected sinogram). In certain implementations, the loss function may be a mean squared error (MSE) of the voxel-level values or partial-line-integral values (e.g., between reconstructed images derived from the measured sinogram and the corrected sinogram) and/or may account for differences involving other image features, such as image gradients or other image statistics. Alternatively, the loss function 62 could be defined by other metrics associated (e.g., structural similarity index measure (SSIM)) with the particular task in question, such as a softmax function. As described in greater detail below, a hybrid domain loss function may be utilized during training (e.g., loss in a sinogram domain and loss in an image reconstruction domain). The following losses may also be utilized. In the sinogram domain, content loss may be utilized (e.g., L1 and/or L2 losses are computed between target and predicted sinograms). Perceptual loss may be utilized (e.g., SSIM loss computed between sinogram and reconstruction domains). Transform domain loss may be utilized (e.g., the loss can be computed over filtered domain/wavelet domain) in the sinogram domain or the image reconstruction domain. Also, adversarial loss can also be used in the training.

In a training example, the neural network 50 may first be constrained to be linear (i.e., by removing all non-linear units) to ensure a good initialization of the network parameters. The neural network 50 may also be pre-trained stage-by-stage using computer simulated input-target data sets, as discussed in greater detail below. After pre-training, the neural network 50 may be trained as a whole and further incorporate non-linear units.

To facilitate explanation of the present image analysis approach using deep learning techniques, the present disclosure discusses these approaches in the context of a CT system. However, it should be understood that the following discussion may also be applicable to other image modalities and systems including, but not limited to, PET, CT, CBCT, PET-CT, SPECT, multi-spectral CT, as well as to non-medical contexts or any context where tomographic reconstruction is employed to reconstruct an image.

Figure 2:
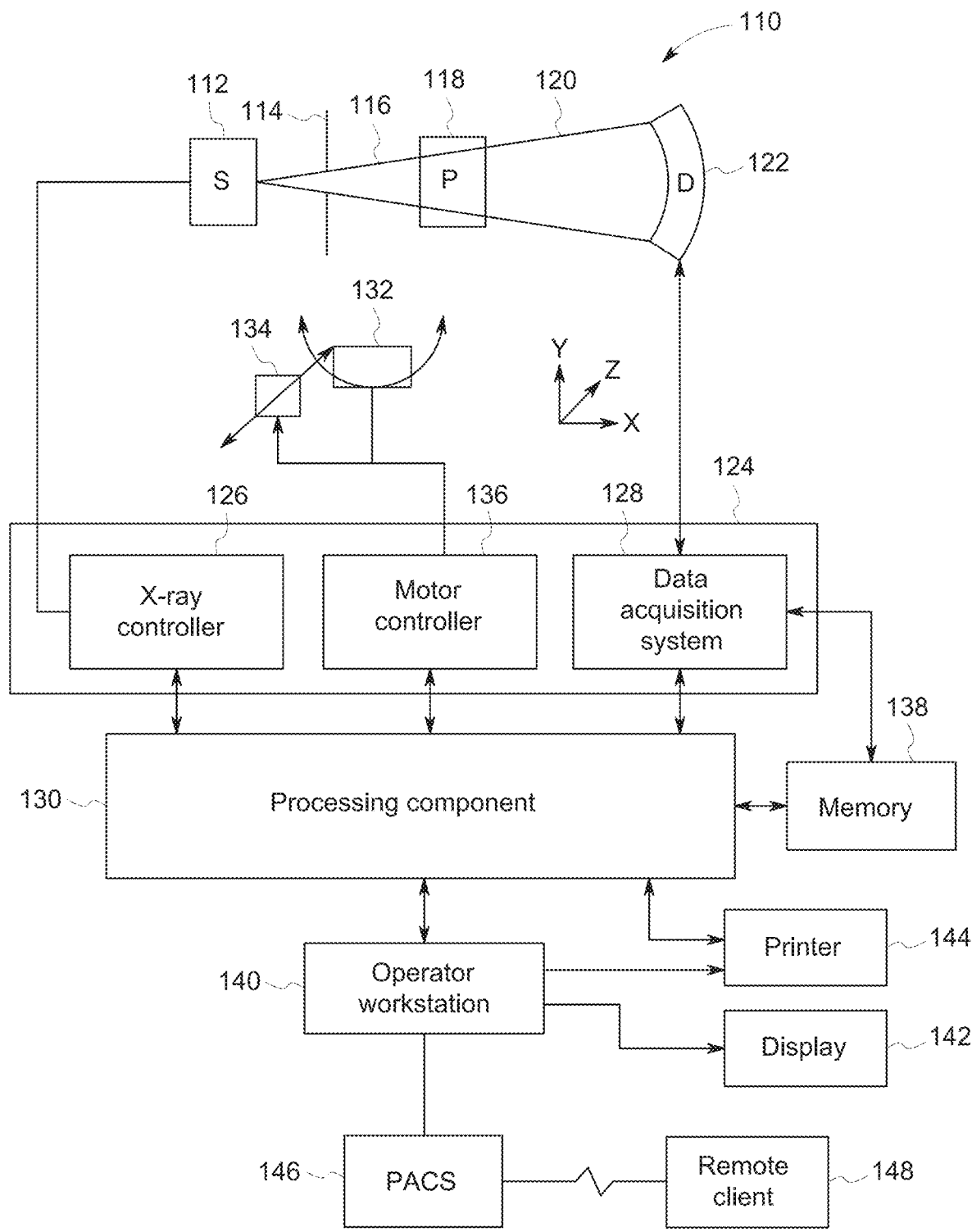
FIG. 2 is a block diagram depicting components of a computed tomography (CT) imaging system, in accordance with aspects of the present disclosure.

With this in mind, an example of a CT imaging system 110 (i.e., a CT scanner) is depicted in FIG. 2. In the depicted example, the imaging system 110 is designed to acquire scan data (e.g., X-ray attenuation data) at a variety of views around a patient (or other subject or object of interest) and suitable for performing image reconstruction using tomographic reconstruction techniques. In the embodiment illustrated in FIG. 2, imaging system 110 includes a source of X-ray radiation 112 positioned adjacent to a collimator 114. The X-ray source 112 may be an X-ray tube, a distributed X-ray source (such as a solid-state or thermionic X-ray source) or any other source of X-ray radiation suitable for the acquisition of medical or other images.

In the depicted example, the collimator 114 shapes or limits a beam of X-rays 116 that passes into a region in which a patient/object 118, is positioned. In the depicted example, the X-rays 116 are collimated to be a cone-shaped beam, i.e., a cone-beam, that passes through the imaged volume. A portion of the X-ray radiation 120 passes through or around the patient/object 118 (or other subject of interest) and impacts a detector array, represented generally at reference numeral 122. Detector elements of the array produce electrical signals that represent the intensity of the incident X-rays 120. These signals are acquired and processed to reconstruct images of the features within the patient/object 118.

Source 112 is controlled by a system controller 124, which furnishes both power, and control signals for CT examination sequences, including acquisition of two-dimensional localizer or scout images used to identify anatomy of interest within the patient/object for subsequent scan protocols. In the depicted embodiment, the system controller 124 controls the source 112 via an X-ray controller 126 which may be a component of the system controller 124. In such an embodiment, the X-ray controller 126 may be configured to provide power and timing signals to the X-ray source 112.

Moreover, the detector 122 is coupled to the system controller 124, which controls acquisition of the signals generated in the detector 122. In the depicted embodiment, the system controller 124 acquires the signals generated by the detector using a data acquisition system 128. The data acquisition system 128 receives data collected by readout electronics of the detector 122. The data acquisition system 128 may receive sampled analog signals from the detector 122 and convert the data to digital signals for subsequent processing by a processor 130 discussed below. Alternatively, in other embodiments the digital-to-analog conversion may be performed by circuitry provided on the detector 122 itself. The system controller 124 may also execute various signal processing and filtration functions with regard to the acquired image signals, such as for initial adjustment of dynamic ranges, interleaving of digital image data, and so forth.

In the embodiment illustrated in FIG. 2, system controller 124 is coupled to a rotational subsystem 132 and a linear positioning subsystem 134. The rotational subsystem 132 enables the X-ray source 112, collimator 114 and the detector 122 to be rotated one or multiple turns around the patient/object 118, such as rotated primarily in an x, y-plane about the patient. It should be noted that the rotational subsystem 132 might include a gantry or C-arm upon which the respective X-ray emission and detection components are disposed. Thus, in such an embodiment, the system controller 124 may be utilized to operate the gantry or C-arm.

The linear positioning subsystem 134 may enable the patient/object 118, or more specifically a table supporting the patient, to be displaced within the bore of the CT system 110, such as in the z-direction relative to rotation of the gantry. Thus, the table may be linearly moved (in a continuous or step-wise fashion) within the gantry to generate images of particular areas of the patient 118. In the depicted embodiment, the system controller 124 controls the movement of the rotational subsystem 132 and/or the linear positioning subsystem 134 via a motor controller 136.

In general, system controller 124 commands operation of the imaging system 110 (such as via the operation of the source 112, detector 122, and positioning systems described above) to execute examination protocols and to process acquired data. For example, the system controller 124, via the systems and controllers noted above, may rotate a gantry supporting the source 112 and detector 122 about a subject of interest so that X-ray attenuation data may be obtained at one or more views relative to the subject. In the present context, system controller 124 may also include signal processing circuitry, associated memory circuitry for storing programs and routines executed by the computer (one or more neural networks (e.g., multi-channel sinogram correction network)), as well as configuration parameters, image data, and so forth.

In the depicted embodiment, the image signals acquired and processed by the system controller 124 are provided to a processing component 130 for reconstruction of images. The processing component 130 may be one or more general or application-specific microprocessors. The data collected by the data acquisition system 128 may be transmitted to the processing component 130 directly or after storage in a memory 138. Any type of memory suitable for storing data might be utilized by such an exemplary system 110. For example, the memory 138 may include one or more optical, magnetic, and/or solid state memory storage structures. Moreover, the memory 138 may be located at the acquisition system site and/or may include remote storage devices for storing data, processing parameters, and/or routines for tomographic image reconstruction and analysis, as described below.

The processing component 130 may be configured to receive commands and scanning parameters from an operator via an operator workstation 140, typically equipped with a keyboard and/or other input devices. An operator may control the system 110 via the operator workstation 140. Thus, the operator may observe the reconstructed images and/or otherwise operate the system 110 using the operator workstation 140. For example, a display 142 coupled to the operator workstation 140 may be utilized to observe the reconstructed images and to control imaging. Additionally, the images may also be printed by a printer 144 which may be coupled to the operator workstation 140.

Further, the processing component 130 and operator workstation 140 may be coupled to other output devices, which may include standard or special purpose computer monitors and associated processing circuitry. One or more operator workstations 140 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 140 may also be coupled to a picture archiving and communications system (PACS) 146. PACS 146 may in turn be coupled to a remote client 148, radiology department information system (RIS), hospital information system (HIS) or to an internal or external network, so that others at different locations may gain access to the raw or processed image data.

While the preceding discussion has treated the various exemplary components of the imaging system 110 separately, these various components may be provided within a common platform or in interconnected platforms. For example, the processing component 130, memory 138, and operator workstation 140 may be provided collectively as a general or special purpose computer or workstation configured to operate in accordance with the aspects of the present disclosure. In such embodiments, the general or special purpose computer may be provided as a separate component with respect to the data acquisition components of the system 110 or may be provided in a common platform with such components. Likewise, the system controller 124 may be provided as part of such a computer or workstation or as part of a separate system dedicated to image acquisition.

As discussed herein, the system 110 of FIG. 2 may be used to conduct a CT scan by measuring a series of views or projections from many different angles around the patient 118 or object. Each view has a transaxial dimension and a longitudinal dimension that correspond to the number of columns and rows, respectively of the CT detector 122. The projections acquired at different view angles can be combined into a sinogram, which collects the multiple views into a single data set. The sinogram represents the spatial distribution of the X-ray attenuation coefficient within the patient. Typically, the sinogram represents the spatial distribution of the X-ray attenuation coefficient over the full rotation of the CT gantry (e.g., at a single axial position). A reconstruction algorithm processes the sinogram to produce a space-domain image representing the patient 118 or object.

Figure 3:
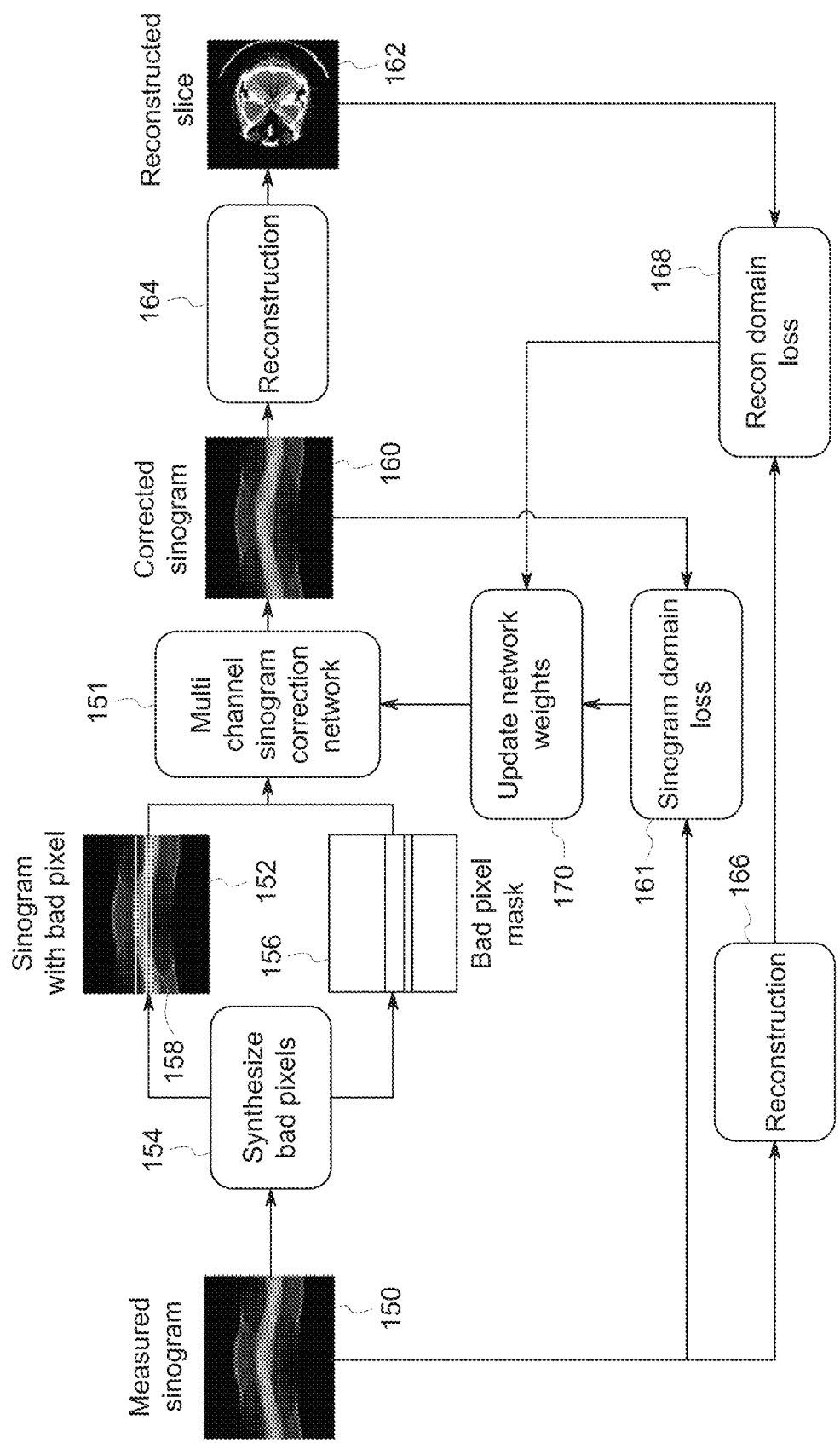
FIG. 3 is a schematic diagram depicting the training of a neural network to correct for a bad pixel, in accordance with aspects of the present disclosure.

As discussed above, the CT detector may have one or more bad pixels that may result in artifacts in the reconstructed images. FIG. 3 is a schematic diagram depicting the training of a neural network to correct for a bad pixel. To generate training data for training a neural network (multi-channel sinogram correction network) 151, a measured sinogram 150 (a good sinogram that is not missing any values for any pixels) is obtained utilizing the CT imaging system described above. From the measured sinogram 150, a simulated sinogram 152 with a bad pixel is generated synthesis of bad pixels 154. For example, a bad pixel mask 156 is utilized to simulate the bad pixel at a random location within the measured sinogram 150. The bad pixel is represented by one or more lines 158 in the simulated sinogram 152 which lack any pixel values for a specific detector pixel.

One or more bad pixels may be simulated in the simulated sinogram 152. The simulated bad pixels may be in separate locations or grouped together in a particular location. In certain embodiments, the simulated bad pixels may correspond to the central region (isocenter) of the CT detector. The bad pixel mask 156 and corresponding simulated sinogram 152 (e.g., as a patch) are provided as inputs to the multi-channel sinogram correction network 151. The network 151 learns to predict the missing pixel value(s) in the simulated sinograms 152. In particular, the network 151 learns to predict the missing pixel value(s) from complementary information available in the sinogram 152. The complementary information is fed in the form of multi-channel input data (e.g., multi-channel two-dimensional (2D) or three-dimensional (3D) patches) to the network 151 as described in greater detail below. When multiple views are utilized a 3D patch may be utilized. The complementary information may include local neighborhood sinogram information and conjugate sinogram information (e.g., information from a conjugate region relative to the location of the bad pixel (e.g., 180 degrees away from the bad pixel location along the CT detector)).

A corrected (e.g., estimated or predicted) sinogram (e.g., as a patch) 160 may be outputted by the network 151. The corrected sinogram or sinogram patch 160 may be compared to the measured sinogram or sinogram patch 150 (which serves as the ground truth) to determine the training loss in the sinogram domain 161. The sinogram domain loss 161 may be in the form of MAE loss. The sinogram loss 161 may be in the form of content loss (e.g., L1 and/or L2 losses are computed between target and predicted sinograms). In certain embodiments, the sinograms 152 may be provided to the network 151 as a raw sinogram. In certain embodiments, the sinogram 152 may be transformed (e.g., filtered) prior to being provided to the network 151. Correction may then be performed in the transformed domain (e.g., wavelet domain) before eventually being transformed back to the normal or native sinogram domain and outputted. Processing the sinogram in the transform domain highlights detail features that drive the training and enhancing the sinogram domain loss.

A tomographic image or volume 162 is generated from the corrected sinogram 160 via reconstruction 164. In addition, a tomographic image or volume is generated from the measured sinogram 150 via reconstruction 166. Patches of the tomographic image or volume 162 is compared to patches of the tomographic image or volume (which serves as the ground truth) generated from the measured sinogram 150 to determine the training loss in the image reconstruction domain 168. The image reconstruction domain loss 168 may be in the form of MSE loss or SSIM. Other losses may be utilized. For example, perceptual loss may be utilized (e.g., SSIM loss computed between sinogram and reconstruction domains). Transform domain loss may be utilized (e.g., the loss can be computed over filtered domain/wavelet domain) in the sinogram domain or the image reconstruction domain. Also, adversarial loss can also be used in the training.

Training weights (network weights) are updated (as indicated by reference numeral 170) at least via the sinogram domain loss 161. In certain embodiments, updating of the training weights occurs 170 occurs via a dual domain loss function utilizing both the sinogram domain loss 161 and the image reconstruction domain loss 168. In certain embodiments, a single correction network utilizes the dual domain loss function. In other embodiments, separate correction networks may be utilized in a serial manner. For example, a first network (e.g., sinogram domain correction network) that corrects the sinogram having the bad pixel data based on loss defined in the native (raw) or transformed domain of the sinogram may be utilized. Then, a second network (e.g., image reconstruction domain correction network) that corrects for any perceived artifacts in the reconstructed tomographic image derived from the corrected sinogram to improve the final image based on the reconstruction domain loss may be utilized.

Figure 4:
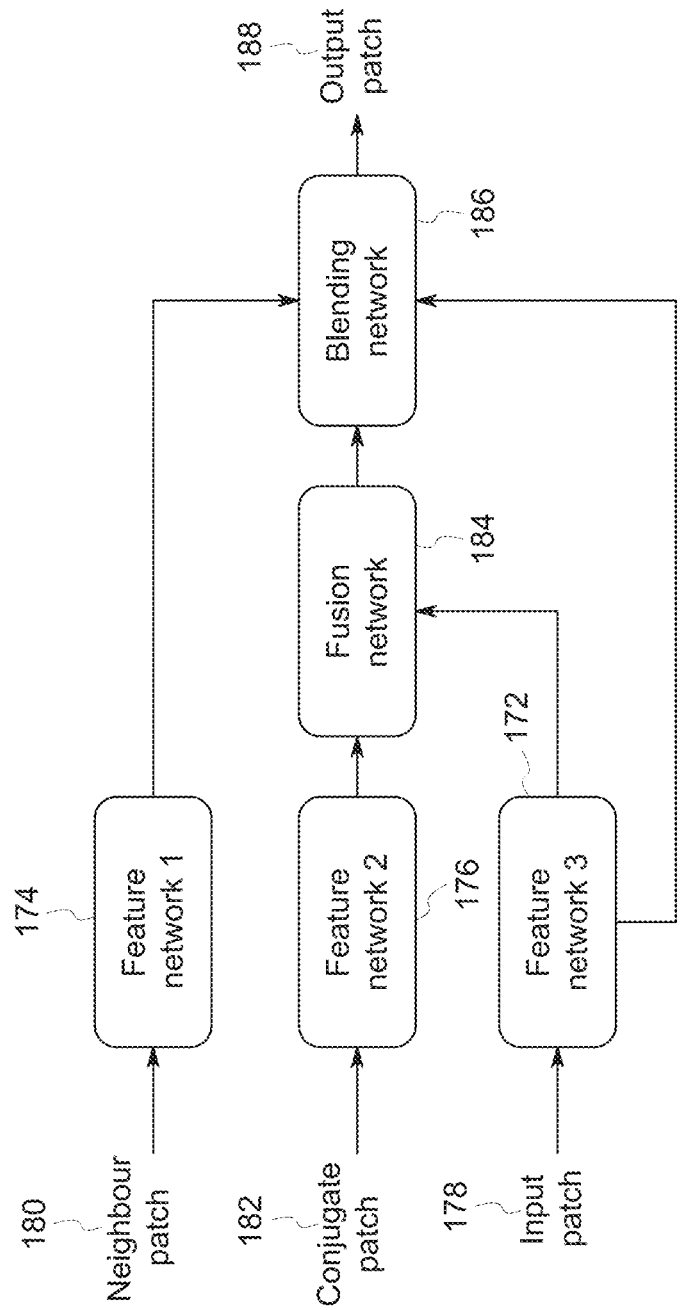
FIG. 4 is a schematic diagram depicting a multi-channel sinogram correction network, in accordance with aspects of the present disclosure.

As mentioned above, the multi-channel sinogram correction network 151 learns to predict the missing pixel value(s) from complementary information available in the sinogram with the missing pixel value(s). FIG. 4 is a schematic diagram depicting the multi-channel sinogram correction network 151 that is trained and eventually utilized to correct for predicting missing pixel values in sinograms that lack data due to bad pixels. As depicted, the network 151 may include multiple networks (e.g., feature networks 172, 174, 176; fusion network 184; blending network 186). Complementary information is fed in the form of multi-channel input data (e.g., multi-channel 2D or 3D patches) to the network 151. In certain embodiments, some of the networks may be 2D-CNN networks.

An input patch 178 is derived from the sinogram missing the pixel value(s) for at least one bad pixel. The input patch 178 is a local neighborhood patch from the bad sinogram within the vicinity of the bad pixel (e.g., corresponding to a portion along a channel view direction of a row having the bad pixel). The local neighborhood path exploits the spatial correlation within the neighboring channels and views. The input patch 178 is inputted into the feature network 172.

A neighbor patch 180 (e.g., neighboring row patch) is derived from the portion of the bad sinogram corresponding to an adjacent row to the row having the bad pixel. The neighbor row patch exploits the neighboring sensor correlation in the z-direction. The neighbor patch 180 is inputted into the feature network 174.

A conjugate patch 182 is derived from a conjugate region of the bad sinogram that is relative the bad pixel. For example, a conjugate region of the sinogram may contain data acquired at a pixel location 180 degrees away from the bad pixel location along the CT detector. The conjugate patch 182 exploits the complementary information available due to the CT geometry. The conjugate patch 182 is inputted into the feature network 176.

The data outputted from feature network 176 and feature network 172 are combined in the fusion network 84 (e.g., via data concatenation). It should be noted that the feature networks 172, 176 and fusion network 184 may utilize deep residual learning in learning to estimate a pixel value for the missing pixel value in the bad sinogram due to the bad pixel. The output of the fusion network 184 along with the outputs from the feature networks 172, 174 are utilized in the blending network 186 to generate an output patch 188 for the corrected sinogram. In certain embodiments, the blending network 186 may generate the output patch via mask addition (e.g., generating a mask that includes the pixel value that is applied to the patch missing the pixel value).

Besides the complementary information provided via the patches 178, 180, 182, other inputs that provide complementary information for the training of the multi-channel sinogram correction network 151. For example, in the case of a dual energy CT scan, the second energy scan be used as an input channel. Also, alternative patches may be utilized that include a different definition of similarity that is based on a user defined neighborhood.

Figure 5:
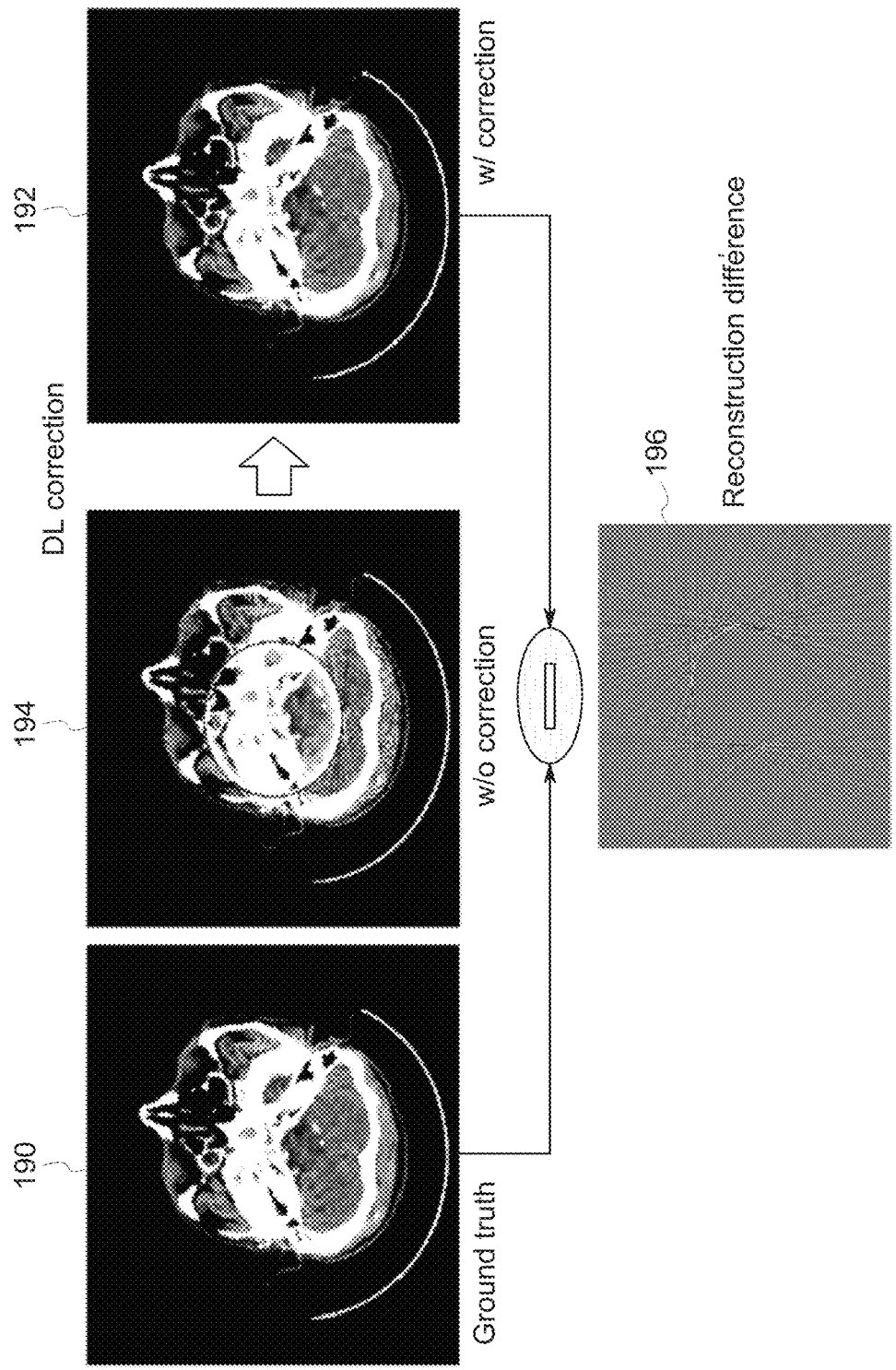
FIG. 5 is a schematic diagram depicting reconstruction domain analysis for determining image reconstruction domain loss, in accordance with aspects of the present disclosure.

As mentioned above, training the neural network involves determining the training loss in the image reconstruction domain. FIG. 5 is a schematic diagram depicting reconstruction domain analysis for determining image reconstruction domain loss. A reconstructed image 190 derived from a good sinogram (i.e., not missing a pixel value due to a bad pixel) is utilized as a ground truth. A reconstructed image 192 is derived from a corrected sinogram (e.g., estimated sinogram with estimated or predicted pixel value for bad pixel) that was outputted from the sinogram correction network. Reconstructed image 194 derived from the uncorrected or bad sinogram (e.g., having the missing pixel value) has a ring artifact. The reconstructed image 194 have the ring artifact. The reconstructed image 192 is compared to the ground truth (reconstructed image 190) to determine a reconstruction difference 196 (e.g., the image reconstruction domain training loss). In certain embodiments, patches of the images 190, 192 may be compared to determine the image reconstruction domain training loss. In certain embodiments, the image domain may be transformed (e.g., filtered) into a different domain prior to performing reconstruction domain loss analysis. As mentioned above, this training loss 196 is utilized to update the training weights utilized in training the sinogram correction network as part of a dual domain or hybrid domain loss. In certain embodiments, a separate network (separate from the sinogram correction network) may be utilized (e.g., in a serial manner) to correct for any artifacts (e.g., ring artifacts) still present in a reconstructed image generated from a corrected sinogram. The separate network may learn utilizing the image reconstruction domain loss.

Figure 6:
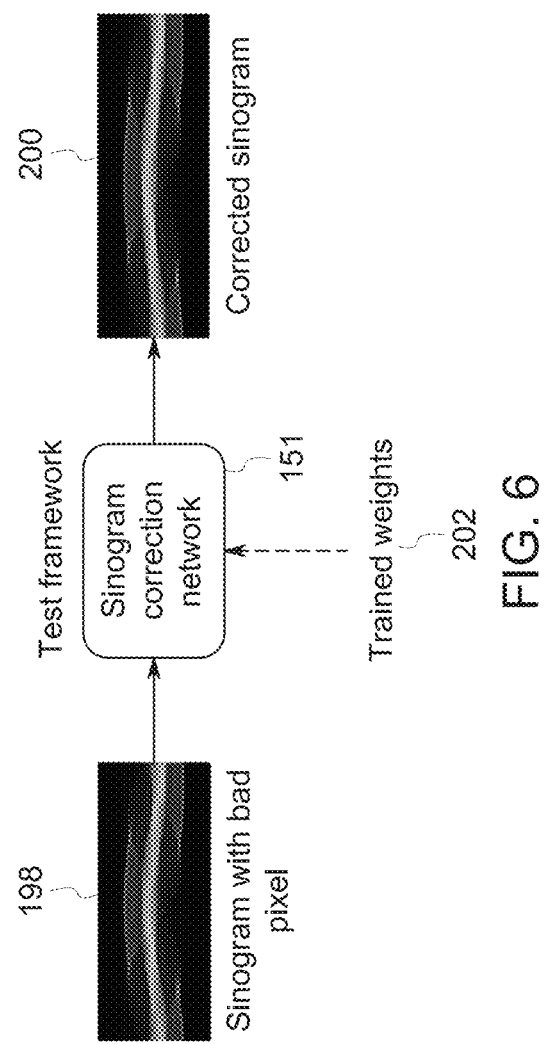
FIG. 6 is a schematic diagram depicting the utilization of a trained sinogram correction network, in accordance with aspects of the present disclosure.

FIG. 6 is a schematic diagram depicting the utilization of a trained sinogram correction network. The trained multi-channel sinogram correction network or model 151 is configured to receive a bad sinogram 198 (i.e., a sinogram missing a pixel value due to a bad pixel) and output a corrected sinogram 200. Pixel values are inferred (e.g., predicted or estimated) for any missing pixels values in the bad sinogram 198. In particular, trained weights 202 are utilized by the network 151 in inferring the missing pixel value(s). The trained weights 202 may have been adjusted by at least the sinogram domain training loss as noted above. In certain embodiments, both the sinogram domain training loss and the image reconstruction domain loss were utilized in updating the trained weights. Multi-channel data (e.g., 2D or 3D patches) are inputted into the network. Correction solely occurs in the sinogram domain. The network 151 is solely dependent on the inputted patches in the sinogram domain. There is no need to go into the reconstruction domain. Thus, the transformation is independent of anatomy, display field of view or reconstruction field of view, and reconstruction parameters (including reconstruction kernel). Since the process is independent of reconstruction parameters, there is no need for tuning parameters. As noted above, the network 151 may work in the raw sinogram domain or a transformed (e.g., filtered) domain of the sinogram. With the inferencing occurring completely in the sinogram domain, it enables faster prediction.

In certain embodiments, as noted above, separate correction networks may be utilized in a serial manner. For example, a first network (e.g., sinogram domain correction network) that corrects the sinogram having the bad pixel data may be utilized followed by a second network (e.g., image reconstruction domain correction network) that corrects for any perceived artifacts (ring or streak artifacts) in the reconstructed tomographic image derived from the corrected sinogram to improve the final image.

The trained network 151 in FIG. 6 was trained with data from 40 exams which resulted in approximately 500,000 multi-channel training patches (neighbor, row, conjugate). For the ground truth, patches were taken from a good sinogram (with missing data from a bad pixel and a reconstructed image from the good sinogram. Of the 40 exams, 32 exams were utilized for training and 8 exams were utilized for validation. The training parameters includes 1000 epochs, a learning rate of $2 \times 10^{-40}$ with a LR decay function of $5 \times 10^{-4} * 0.1^{epoch/100}$, and a loss function of MAE+SSIM.

Figure 7:
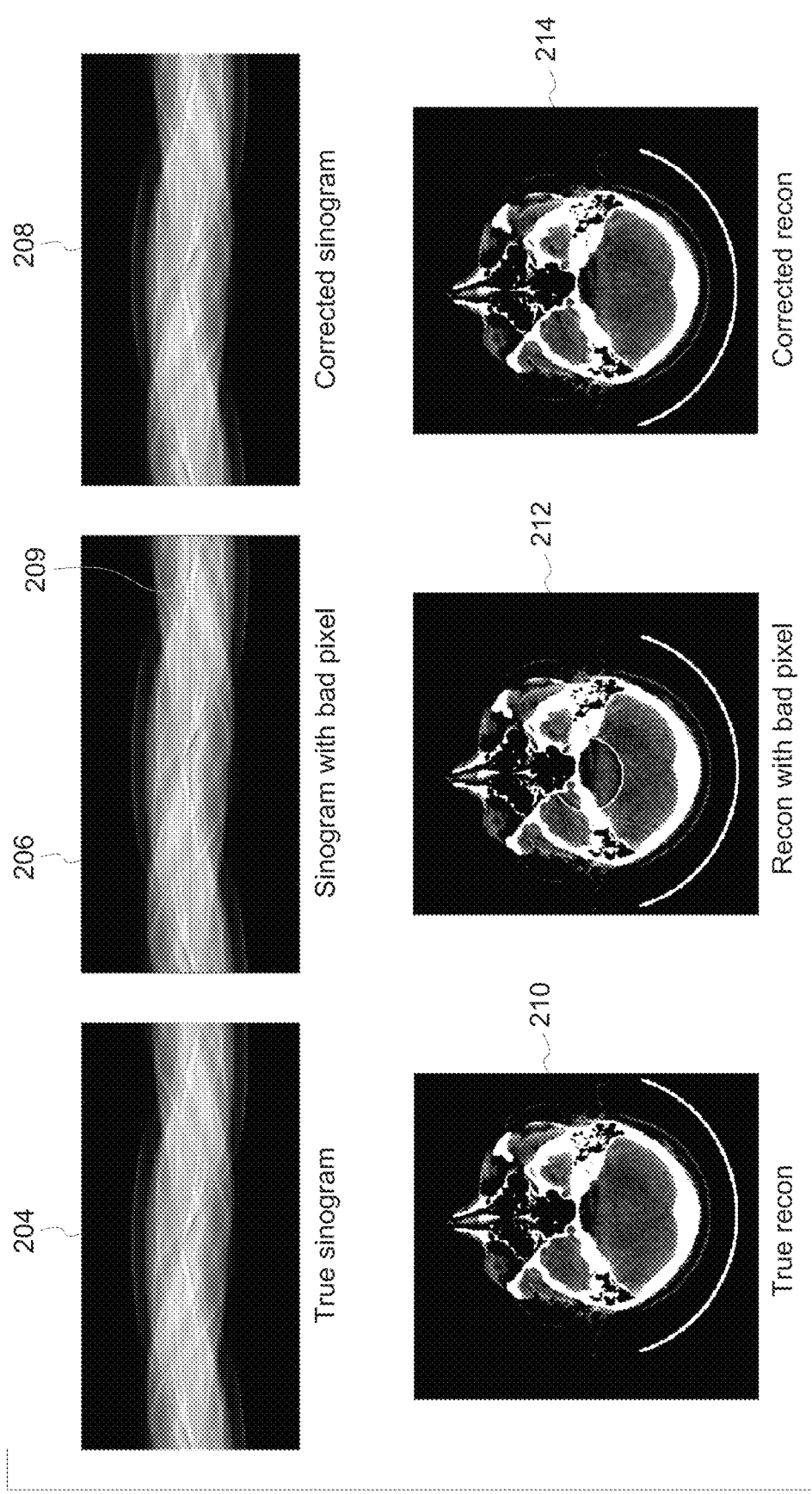
FIG. 7 depicts different types of sinograms and corresponding image reconstructions, in accordance with aspects of the present disclosure.

FIG. 7 depicts different types of sinograms and corresponding image reconstructions. Sinograms 204, 206, 208 represent a true sinogram (i.e., without any missing values due to a bad pixel), a bad sinogram missing a pixel value as indicated by line 209 due to a bad pixel, and a corrected sinogram outputted utilizing the deep learning-based sinogram correction model discussed above. As depicted in the sinogram 208, the line 209 in sinogram 206 is no longer present as a pixel value has been estimated for the missing pixel value. Reconstructed images 210, 212, and 214 represent the corresponding images derived from sinograms 204, 206, and 208. As depicted in the image 212, ring and streak artifacts are present due to the missing data from the bad pixel. As depicted in the image 214, the ring and streak artifacts are absent and the image 214 looks similar to image 210.

Technical effects of the disclosed subject matter include providing a deep learning-based technique for correcting missing pixel value(s) due to one or more bad pixels in a CT detector. Multi-channel input data having complementary information in the sinogram is utilized in a trained network to predict the missing pixel value. In particular, predicting the missing pixel value occurs completely in the sinogram domain to provide a faster prediction. Correction occurs solely in the sinogram domain making the process independent of anatomy, display field of view, and reconstruction parameters (including reconstruction kernel). By correcting for bad pixels, the deep-learning based technique provides quality reconstructed images lacking ring and streak artifacts due to bad detector pixels that suitable for diagnostic purposes. The deep-learning based technique enables the relaxation in constraints during production of CT detectors and utilization of the CT detectors in the field. In particular, CT detectors with a bad pixel in a central region of the detector or multiple bad pixels in general on the detector may still be utilized. This may reduce service costs (e.g., associated with detector panel replacement) due to bad pixels.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method for correcting artifacts in computed tomography data, comprising:
inputting a sinogram into a trained sinogram correction network, wherein the sinogram is missing a pixel value for at least one pixel;
processing the sinogram via one or more layers of the trained sinogram correction network, wherein processing the sinogram comprises deriving complementary information from the sinogram and estimating the pixel value for the at least one pixel based on the complementary information, wherein the complementary information comprises multi-channel patches, and the multi-channel patches comprise a local neighborhood patch from the sinogram corresponding to a portion along a channel-view direction of a row having the at least one pixel, a neighboring row patch from the sinogram corresponding to an adjacent row to the row having the at least one pixel, and a conjugate patch from the sinogram corresponding to a conjugate region relative to the at least one pixel; and outputting from the trained sinogram correction network a corrected sinogram having the estimated pixel value.

2. The computer-implemented method of claim 1, comprising reconstructing an image from the corrected sinogram with reduced artifacts.

3. The computer-implemented method of claim 1, wherein the sinogram is a raw projection data measurement captured by the detector of X-Ray computed tomography system.

4. The computer-implemented method of claim 1, comprising training a neural network using supervised learning to generate the trained sinogram correction network, wherein training data used for the supervised learning comprises sinograms without any missing pixel values and corresponding sinograms with missing pixel values simulated from the sinograms without any missing pixel values.

5. The computer-implemented method of claim 4, wherein a training loss is derived from at least a sinogram domain of the training data.

6. The computer-implemented method of claim 5, wherein the training loss is derived from both the sinogram domain of the training data and an image reconstruction domain of images reconstructed from the training data.

7. The computer-implemented method of claim 6, wherein the corresponding sinograms with missing pixel values of the training data are corrected after determining the training loss from both the sinogram domain of the training data and the image reconstruction domain of the images reconstructed from the training data.

8. The computer-implemented method of claim 6, wherein the corresponding sinograms with missing pixel values of the training data are corrected after determining a sinogram-domain training loss from the sinogram domain of the training data and then corrected sinograms of the corresponding sinograms with missing pixel values are reconstructed into the images from which an image-reconstruction domain training loss is determined to improve the images.

9. The computer-implemented method of claim 4, wherein the training data may be raw, transformed, or a combination thereof.

10. A computer-implemented method for generating a trained neural network to estimate missing values in computed tomography data, comprising:

providing training data comprising sinograms and complementary information derived from the sinograms, wherein the sinograms comprise sinograms without any missing pixel values and corresponding sinograms with missing pixel values simulated from the sinograms without any missing pixel values; and training, using the training data, a neural network to correct a sinogram having a pixel value missing for at least one pixel based on utilizing a combined training loss derived from both the sinogram domain of the training data and an image reconstruction domain of images reconstructed from the training data.

11. The computer-implemented method of claim 10, wherein the complementary information comprises multi-channel patches derived from each of the sinograms with missing pixel values.

12. The computer-implemented method of claim 11, wherein the multichannel patches for a respective sinogram with a missing pixel value comprise a local neighborhood patch corresponding to a portion along a channel-view direction of a row having the missing pixel value, a neighboring row patch corresponding to an adjacent row to the row having the missing pixel value, and a conjugate patch corresponding to a conjugate region relative to the missing pixel value.

13. The computer-implemented method of claim 10, wherein the training data is raw, transformed, or a combination thereof.

14. The computer-implemented method of claim 10, wherein training the neural network to correct the sinogram having the pixel value missing for the at least one pixel comprises training the neural network to estimate the pixel value independent of anatomy of an object scanned, a display field of view, and reconstruction parameters utilized to reconstruct the sinogram into a reconstructed image.

15. The computer-implemented method of claim 10, comprising wherein, during the training, the corresponding sinograms with missing pixel values of the training data are corrected after determining a combined training loss.

16. The computer-implemented method of claim 10, comprising wherein, during the training, the corresponding sinograms with missing pixel values of the training data are corrected after determining a sinogram-domain training loss from the sinogram domain of the training data and then corrected sinograms of the corresponding sinograms with missing pixel values are reconstructed into the images from which an image reconstruction domain training loss is determined to improve the images.

17. A deep learning-based sinogram correction system, comprising:

a memory encoding processor-executable routines;

a processing component configured to access the memory and to execute the processor- executable routines, wherein the routines, when executed by the processing component, cause the processing component to:

input a sinogram into a trained sinogram correction network, wherein the sinogram is missing a pixel value for at least one pixel;

process the sinogram via one or more layers of the trained sinogram correction network, wherein processing the sinogram comprises deriving complementary information from the sinogram and estimating the pixel value for the at least one pixel based on the complementary information, wherein the complementary information comprises multichannel patches, and the multi-channel patches comprise a local neighborhood patch from the sinogram corresponding to a portion along a channel-view direction of a row having the at least one pixel, a neighboring row patch from the sinogram corresponding to an adjacent row to the row having the at least one pixel, and a conjugate patch from the sinogram corresponding to a conjugate region relative to the at least one pixel; and output from the trained sinogram correction network a corrected sinogram having the estimated pixel value.

18. The system of claim 17, wherein the routines, when executed by the processing component, cause the processing component to train a neural network using supervised learning to generate the trained sinogram correction network, wherein training data used for the supervised learning comprises sinograms without any missing pixel values and corresponding sinograms with missing pixel values simulated from the sinograms without any missing pixel values, and wherein the training loss is derived either only from sinogram domain of the training data or from both a sinogram domain and an image reconstruction domain of images reconstructed from the training data.

* * * * *